(12) United States Patent
Embse et al.

(10) Patent No.: US 8,865,920 B2
(45) Date of Patent: Oct. 21, 2014

(54) N-ACYLATION OF AMINES

(75) Inventors: Richard Vonder Embse, St. Charles, MO (US); Michael Hayes, St. Charles, MO (US); James C. Peterson, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 13/581,887

(22) PCT Filed: Mar. 9, 2011

(86) PCT No.: PCT/US2011/027641
§ 371 (c)(1),
(2), (4) Date: Sep. 21, 2012

(87) PCT Pub. No.: WO2011/112648
PCT Pub. Date: Sep. 15, 2011

(65) Prior Publication Data
US 2013/0012728 A1    Jan. 10, 2013

Related U.S. Application Data

(60) Provisional application No. 61/312,012, filed on Mar. 9, 2010, provisional application No. 61/312,020, filed on Mar. 9, 2010, provisional application No. 61/312,024, filed on Mar. 9, 2010, provisional application No. 61/333,915, filed on May 12, 2010.

(51) Int. Cl.
    C07D 307/00    (2006.01)
    C07C 229/00    (2006.01)
    C07C 231/00    (2006.01)
    C07C 319/14    (2006.01)
    C07C 391/00    (2006.01)
    C07D 265/10    (2006.01)

(52) U.S. Cl.
    CPC ............. C07C 319/14 (2013.01); C07C 391/00 (2013.01); C07D 265/10 (2013.01)
    USPC ........................... 549/321; 562/575; 564/138

(58) Field of Classification Search
    CPC ........................... C07D 307/00; C07C 231/00
    USPC ........................... 564/138; 562/575; 549/321
    See application file for complete search history.

(56) References Cited

U.S. PATENT DOCUMENTS

| | | |
|---|---|---|
| 5,344,767 A | 9/1994 | Boullais et al. |
| 6,080,769 A | 6/2000 | Lyssikatos et al. |
| 6,194,616 B1 | 2/2001 | Spagnol et al. |
| 6,215,024 B1 * | 4/2001 | Choudary et al. ............. 564/138 |
| 7,368,600 B2 | 5/2008 | Hateley et al. |
| 7,381,416 B2 | 6/2008 | Erdelmeir et al. |
| 7,884,240 B2 | 2/2011 | Hateley et al. |
| 7,906,513 B2 | 3/2011 | Moore et al. |
| 2003/0083383 A1 | 5/2003 | Spallholz et al. |
| 2005/0101669 A1 | 5/2005 | Klatt et al. |
| 2007/0190622 A1 | 8/2007 | Hateley et al. |
| 2010/0055291 A1 | 3/2010 | Erdelmeier et al. |
| 2011/0224430 A1 | 9/2011 | Lorbert |
| 2011/0224458 A1 | 9/2011 | Lorbert |

FOREIGN PATENT DOCUMENTS

| | | |
|---|---|---|
| CN | 101223134 A | 7/2008 |
| CN | 101573367 A | 11/2009 |
| EP | 07782361 A1 | 11/1997 |
| JP | 1989502021 A | 7/1989 |
| JP | 1999236333 A | 8/1999 |
| JP | 2001002668 A | 1/2001 |
| JP | 2009524615 A | 7/2009 |
| WO | 8705909 | 10/1987 |
| WO | 9606068 | 2/1996 |
| WO | 2007011563 A1 | 1/2007 |
| WO | 2008127240 A1 | 10/2008 |

OTHER PUBLICATIONS

Dorwald F. A. Side Reactions in Organic Synthesis, 2005, Wiley: VCH, Weinheim p. IX of Preface p. 1-15.*
Office action dated Dec. 31, 2012 from related U.S. Appl. No. 13/043,740, 7 pgs.
Ates-Alagoz, Synthesis and Antioxidant Activity of New Tetrahydro-Naphthalene-Indole Derivatives as Retinoid and Melatonin Analogs. Arch. Pharm. Chem. Life. Sci. 339, 193-200, 2006.
Isaad et al., N-Fmoc Protected w-Azido- and w-Alkynyl-L-amino Acids as Buidling Blocks for the Synthesis of "Clickable" peptides, Eur. J. Org. Chem., 5308-5314, 2008.
Isidro-Llobet, Amino Acid-Protecting Gropus, Chem. Rev., 109, 2455-2504, 2009.
Koch et al., Synthesis of L-(+)-Selenomethionine, Synthesis, 1065-1068, 1993.
Office action from related U.S. Appl. No. 13/043,767 dated Aug. 30, 2013, 25 pages.
Yamamoto et al. An Efficient Oxidation of Long Chain Alkyl Methyl Sulfides to Sulfoxides, Organic Preparations and Procedures International, 32(1), 192-196, 2000.
Zaidlewicz et al., Molecular Addition Compounds. 17. Borane and Chloroborane Adducts with Organic Sulfides for Hydroboration, J. Org. Chem. 65, 6697-6702, 2000.
Extended Search Report for European patent application No. 11753971.8 dated Dec. 4, 2013, 3 pages.
First Office action and Search Report for Chinese patent application No. 201180023378.8 dated Dec. 16, 2013, 33 pages (Translation included).
Office action for Japanese patent application No. 2012-557188 dated Jan. 14, 2014, 6 pages (Translation included).

(Continued)

Primary Examiner — Nizal Chandrakumar
(74) Attorney, Agent, or Firm — Polsinelli PC

(57) ABSTRACT

Provided herein are processes for the preparation of N-acylated amines. In particular, the processes comprise contacting an amine with an acid comprising a carboxylic acid group to form the N-acylated amine.

6 Claims, No Drawings

(56) References Cited

OTHER PUBLICATIONS

Grigg, et al., "XY—ZH compounds as potential 1,3-dipoles. Part 63: Silver catalysed azomethine ylide cycloaddition—the synthesis of spiro homoserine lactone analogues", Tetrahedron, 2006, 62(44), pp. 10332-10343.

Thaisrivongs, et al., "Conformationally Constrained Renin Inhibitory Peptides: [gamma]-Lactam-Bridged Dipeptide Isostere as Conformational Restriction," J. Med. Chem, 1988, 31(7) pp. 1369-1376.

Xuhong, et al., "The protection and application of amino in organic-synthesis", Journal of Shihezi University, vol. 3, No. 1, 1999, as exemplified by the chemical reactions (English abstract included).

Office action for U.S. Appl. No. 13/043,767 dated Aug. 30, 2013, 25 pages.

Issad, et al., "N-Fmoc Protected w-Azido- and w-Alkynyl-L-amino Acids as Building Blocks for the Synthesis of "Clickable" peptides," Eur. J. Org. Chem., 2008, pp. 5308-53014.

Koch et al., "Synthesis of L-(+)-Selenomethionine, Synthesis, 1993, pp. 1065-1068.

Ates-Alagoz, "Synthesis and Antioxidant Activity of New Tetrahydro-Naphthalene-Indole Derivatives as Retinoid and Melatonin Analogs," Arch. Pharm. Chem. Life. Sci. 339, 2006, pp. 193-200.

Yamamoto et al., "An Efficient Oxidation of Long Chain Alkyl Methyl Sulfides to Sulfoxides, Organic Preparations and Procedures International," 32(2), 2000, pp. 192-196.

Isidro-Llobet, et al., "Amino acid-protecting groups", Chem Rev 2009, 109(6) pp. 2455-2504.

Zaidlewicz, et al., "Molecular Addition Compounds. 17. Borane and Chloroborane Adducts with Organic Sulfides for Hydroboration", J. Org. Chem, 2000, 65, pp. 6697-6702.

Office Action for U.S. Appl. No. 13/847,668 dated Dec. 31, 2013 (6 pages).

Notice of Allowance for U.S. Appl. No. 13/043,767 dated Dec. 24, 2013 (9 pages).

Bhanage et al., "Non-catalytic clean synthesis route using urea to cyclic urea and cyclic urethane compounds", Green Chemistry, 2004, pp. 78-80, vol. 6.

Foglino et al., "A direct sulfhydrylation pathway is used for methionine biosynthesis in *Pseudomonas aeruginosa*", Microbiology, 1995, pp. 431-439, vol. 141.

International Search Report and Written Opinion from related International Patent Application No. PCT/US11/27641, dated May 16, 2011, 12 pages.

International Search Report and Written Opinion from related International Patent Application No. PCT/US11/27642, dated May 16, 2011, 13 pages.

Jagtap et al., "Heterogeneous base catalyzed synthesis of 2-oxazolidinones/2-imidiazolidinones via transesterification of ethylene carbonate with beta-aminoalcohols/1,2-diamines", Applied Catalysis A: General, 2008, pp. 133-138, vol. 341.

Karnbrock et al., "A New Efficient Synthesis of Acetyltelluro- and Acetylselenomethionine and Their Use in the Biosynthesis of Heavy-Atom Protein Analogs", Journal of the American Chemical Society, 1996, pp. 913-914, vol. 118, No. 4.

Mohan et al., "Zeolite catalyzed acylation of alcohols and amines with acetic acid under microwave irradiation", Green Chemistry, 2006, pp. 368-372, vol. 8, Abstract Only.

Montalbetti et al., "Amide bond formation and peptide coupling", Tetrahedron, 2005, pp. 10827-10852, vol. 61, No. 46.

Narender et al., "Liquid phase acylation of amines with acetic acid over HY zeolite", Green Chemistry, 2000, pp. 104-105, vol. 2.

Office Action from related U.S. Appl. No. 13/043,740, dated Dec. 31, 2012, 7 pages.

Prasad et al., "Convenient, Cost-Effective, and Mild Method for the N-Acetylation of Anilines and Secondary Amines", Synthetic Communications, 2005, pp. 1189-1195, vol. 35, No. 9.

Selva et al., "A Simple One-Pot Synthesis of Functionalized Ketimines from Ketones and Amine Hydrochloride Salts", Synthetic Communications: An International Journal for Rapid Communication of Synthetic Organic Chemistry, 1995, pp. 369-378, vol. 25, No. 3, Abstract Only.

\* cited by examiner

N-ACYLATION OF AMINES

FIELD OF THE INVENTION

The present invention relates to the preparation of N-acylated amines. In particular, the invention relates to the use of a carboxylic acid-containing acid to mediate the N-acylation reaction.

BACKGROUND OF THE INVENTION

Methionine is utilized in a variety of fields, from pharmaceuticals to health and fitness products to feed supplements. Methionine is produced industrially in large amounts; it is currently produced by a completely synthetic pathway that utilizes petroleum-based chemicals and hazardous chemicals. Because of price increases in petroleum, the high costs associated with hazardous waste management, as well as for safety and environmental reasons, there is a need for alternate methionine synthesis pathways. An attractive starting material is homoserine, which can be converted to methionine via an N-acetylhomoserine lactone intermediate. Current methods for preparing N-acetylhomoserine lactone require the use of reactive acylating agents and catalysts. Because of the cost of these reagents, however, there is a need for cost economical and atom economical processes for the synthesis N-acetylhomoserine lactone from homoserine.

SUMMARY OF THE INVENTION

Among the various aspects of the disclosure is the provision of processes for the preparation of N-acylated amines by contacting the precursor amine with an acid comprising a carboxylic acid group.

Accordingly, provided herein is a process for preparing a compound comprising Formula (II). The process comprises contacting a compound comprising Formula (I) with RCOOH to form the compound comprising Formula (II):

$$R^1-NH_2 \xrightarrow{RCOOH} R^1-\underset{H}{N}-\overset{O}{\underset{\|}{C}}-R$$
(I)                          (II)

wherein:
R, is chosen from hydrogen, hydrocarbyl, and substituted hydrocarbyl; and
$R^1$ is chosen from hydrocarbyl and substituted hydrocarbyl Also provided herein is a process for preparing a compound comprising Formula (IV). The process comprises contacting a compound comprising Formula (III) with RCOOH to form the compound comprising Formula (IV):

(III) → (IV)

wherein:
R is chosen from hydrogen, hydrocarbyl, and substituted hydrocarbyl;
$R^2$ is chosen from hydrocarbyl and substituted hydrocarbyl; and
Z is chosen from O, S, and Se.

Other aspects and features of the disclosure are described in more detail below.

DETAILED DESCRIPTION

Provided herein are processes for the preparation of N-acylated amines. The processes comprise contacting an amine with an acid comprising a carboxylic acid group, wherein, depending on the starting amine compound, the acid mediates 1) acylation of the amino group, or 2) acylation and cyclization of the amino acid. Surprisingly, these processes proceed well in the absence of a catalyst. This discovery permits the preparation of N-acylated amine derivatives or cyclized, N-acylated amino acid derivatives in an efficient and cost effective manner. As an example, the process may be used to prepare N-acetyl homoserine lactone, which is an intermediate useful in the synthesis of methionine.

(I) Preparation of a Compound Comprising Formula (II)

Provided herein is a process for preparing an N-acylated compound comprising Formula (II). The process comprises contacting a compound comprising Formula (I) with RCOOH, wherein the compound comprising Formula (I) undergoes N-acylation to form the compound comprising Formula (II). For the purposes of illustration, Reaction Scheme 1 depicts this aspect of the disclosure:

Reaction Scheme 1:

$$R^1-NH_2 \xrightarrow{RCOOH} R^1-\underset{H}{N}-\overset{O}{\underset{\|}{C}}-R$$
(I)                          (II)

wherein:
R, is chosen from hydrogen, hydrocarbyl, and substituted hydrocarbyl; and
$R^1$ is chosen from hydrocarbyl or substituted hydrocarbyl.

In one embodiment, R may be hydrogen, hydrocarbyl, or substituted hydrocarbyl. In various iterations, R may hydrogen, alkyl, substituted alkyl, haloalkyl, oxoalkyl, carboxy alkyl, aryl, substituted aryl, carboxy aryl, alkenyl, substituted alkenyl, alkynyl, or substituted alkynyl. $R^1$ may be alkyl, substituted alkyl, haloalkyl, oxoalkyl, carboxy alkyl, aryl, substituted aryl, carboxy aryl, alkenyl, substituted alkenyl, alkynyl, or substituted alkynyl.

(a) Reaction Mixture

The process commences with formation of a reaction mixture comprising the compound comprising Formula (I) and RCOOH.

(i) Compound Comprising Formula (I)

A variety of compounds comprising Formula (I) are suitable for use in the process. In general, the compound comprising Formula (I) is a carbon based amine containing compound. In some embodiments, $R^1$ may be chosen from aryl, alkyl, alkenyl, substituted alkyl, or substituted alkenyl, of 1 to 20 carbons. In some embodiments, the compound comprising Formula (I) may be an alpha amino acid, a beta amino acid, a gamma amino acid, and the like. Moreover, the compound comprising Formula (I) may be a natural amino acid, an unnatural amino acid, a standard amino acid, a non-standard amino acid, a proteinogenic amino acid, or a non-proteinogenic amino acid. In other embodiments, the compound comprising Formula (I) may be a primary amine, such as benzylamine, propylamine, ethanolamine, and the like.

(ii) RCOOH

The method comprises contacting the compound comprising Formula (I) with RCOOH. As detailed above, R may be hydrogen, hydrocarbyl, or substituted hydrocarbyl. In some embodiments, R may hydrogen, alkyl, substituted alkyl, haloalkyl, oxoalkyl, carboxy alkyl, aryl, substituted aryl, carboxy aryl, alkenyl, substituted alkenyl, alkynyl, or substituted alkynyl. Thus, RCOOH may be a carboxylic acid, a dicarboxylic acid, or a keto (or oxo) acid. In further embodiments, R may be hydrogen, methyl, ethyl, propyl, butyl, pentyl, phenyl, benzyl, furyl, allyl, mono-, di-, tri-chloroalkyl, mono-, di-, and tri-fluoroalkyl.

Specific examples of RCOOH include formic acid, acetic acid, propionic acid, isopropionic acid, butanoic acid, benzoic acid, allyl acetic acid, chloroacetic acid, dichloroacetic acid, trichloroacetic acid, fluoroacetic acid, difluoroacetic acid, trifluoroacetic acid, oxalic acid, malonic acid, succinic acid, glutaric acid, phthalic acid, isophthalic acid, terephthalic acid, acrylic acid, acetoacetic acid, pyruvic acid, glyceric acid, glycolic acid, and the like. In one embodiment, RCOOH may be acetic acid.

The amount of RCOOH that is contacted with the compound comprising Formula (I) can and will vary. In general, the molar ratio of the compound comprising Formula (I) to RCOOH may range from about 1:1 to about 1:200. In one embodiment, the molar ratio of the compound comprising Formula (I) to RCOOH may range from about 1:5 to about 1:100. In various embodiments, the molar ratio of the compound comprising Formula (I) to RCOOH may be about 1:5, 1:10, 1:15, 1:20, 1:25, 1:30, 1:35, 1:40, 1:45, 1:50, 1:55, 1:60, 1:65, 1:70; 1:75, 1:80, 1:85, 1:90, 1:95, or 1:100. In one embodiment the molar ratio of the compound comprising Formula (I) to RCOOH may be about 1:40.

(iii) Optional Catalyst

In some embodiments, the reaction mixture may further comprise a catalyst. The catalyst may be an ammonium salt comprising an organic moiety, a zeolite mineral, or a clay mineral. In general, the formula of the ammonium salt comprising the organic moiety is $[NH_4]^+[R'COO]^-$, wherein R' is hydrogen, hydrocarbyl, or substituted hydrocarbyl. In some embodiments, R' may be hydrogen, methyl, ethyl, propyl, butyl, pentyl, phenyl, benzyl, furyl, allyl, mono-, di-, tri-chloroalkyl, mono-, di-, or tri-fluoroalkyl. Suitable examples of the ammonium salt include ammonium formate, ammonium acetate, ammonium propionate, ammonium benzoate, ammonium chloroacetate, ammonium dichloroacetate, ammonium trichloroacetate, ammonium fluoroacetate, ammonium difluoroacetate, ammonium trifluoroacetate, and so forth.

Non-limiting examples of zeolite catalysts include analcime, chabazite, clinoptilolite, heulandite, natrolite, phillipsite, and stilbite. Suitable clay catalyst include, without limit, kaolinite, montmoroillonite, illite and chlorite. In some embodiments in which a clay catalyst is used, the process may further comprise contact with microwave irradiation. Those of skill in the art are familiar with appropriate parameters.

The amount of catalyst contacted with the compound comprising Formula (I) and RCOOH can and will vary. In general, the molar ratio of the compound comprising Formula (I) to the catalyst may range from about 1:0.001 to about 1:5. In some embodiments, the molar ratio of the compound comprising Formula (I) to the catalyst may range from about 1:0.005 to about 1:1.

(b) Reaction Conditions

The process is allowed to proceed at a temperature that may range from about 50° C. to about 160° C. In certain embodiments, the temperature of the reaction may be about 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., and 160° C. In one embodiment, the process is conducted at a temperature of about 115° C. In general, the process is conducted under ambient pressure.

The duration of the reaction can and will vary. Typically, the reaction may be allowed to proceed from about 4 hours to about 48 hours. In various embodiments, the duration of the reaction may be about 6 hours, 8 hours, about 10 hours, about 12 hours, about 14 hours, about 16 hours, about 18 hours, about 20 hours, or about 24 hours. In general, the reaction is allowed to proceed for a sufficient period of time until the reaction is substantially complete. The completeness of the reaction may be determined by any method known to one skilled in the art. Suitable methods include IR, HPLC, or LC-MS. In this context, a "completed reaction" generally means that the reaction mixture contains a significantly diminished amount of the compound comprising Formula (I) and a significantly increased amount of the compound comprising Formula (II) compared to the amounts of each present at the beginning of the reaction. Typically, the amount of the compound comprising Formula (I) remaining in the reaction mixture may be less than about 3%, less than about 1%, or preferably less than about 0.5%.

Upon completion of the reaction, the reaction mixture may be cooled and the compound comprising Formula (II) may be isolated by any means familiar to those of skill in the art. Suitable means include distillation, concentration, precipitation, filtration, phase extraction, chromatography, trituration, crystallization, and the like. The isolated product may be washed and dried, and analyzed by means familiar to those skilled in the art.

In some aspects, the reaction mixture further comprises a solvent. Non-limiting examples of solvents include methanol, ethanol, isopropanol, propanol, n-butanol, s-butanol, t-butanol, halogenated solvents, dimethylsulfoxide, water and combinations thereof. In an exemplary embodiment, the solvent may be water.

The yield of the compound comprising Formula (II) can and will vary. Typically, the yield of the compound comprising Formula (II) may be at least about 60% w/w. In some embodiments of the invention, the yield of the compound comprising Formula (II) may be at least about 65%, 70%, 75%, 80%, or 85% w/w. In further embodiments, the yield of the compound comprising Formula (II) may be at least about 90%, 95%, 97%, or 99% w/w.

The compounds comprising Formula (I) or Formula (II) may have L configurations, D configurations, or mixtures thereof.

(II) Preparation of a Compound Comprising Formula (IV)

Also provided herein is a process for preparing a compound comprising Formula (IV). The process comprises contacting a compound comprising Formula (III) with RCOOH, wherein the compound comprising Formula (III) undergoes a cyclization and an N-acylation to form the compound comprising Formula (IV). This aspect of the disclosure is illustrated below in Reaction Scheme 2:

Reaction Scheme 2:

$$\underset{(III)}{H\diagdown_{Z}\diagup^{R^2}\diagdown_{NH_2}\diagup^{O}_{OH}} \xrightarrow{RCOOH} \underset{(IV)}{\overset{R^2}{Z}\square\overset{O}{\underset{O}{\diagdown}}\overset{H}{N}\diagup^{O}_{R}}$$

wherein:
R is chosen from hydrogen, hydrocarbyl, and substituted hydrocarbyl;
R² is chosen from hydrocarbyl and substituted hydrocarbyl; and
Z is chosen from O, S, and Se.

In one embodiment, R may be hydrogen, hydrocarbyl, or substituted hydrocarbyl. In various iterations, R may hydrogen, alkyl, substituted alkyl, haloalkyl, oxoalkyl, carboxy alkyl, aryl, substituted aryl, carboxy aryl, alkenyl, substituted alkenyl, alkynyl, or substituted alkynyl.

In another embodiment, R² may be alkyl, alkenyl, alkynyl, substituted alkyl, substituted alkenyl, or substituted alkynyl. In some iterations, R² may be {—}CH₂{—}, {—}CH₂CH₂{—}, {—}CH(CH₃){—}, {—}CH₂CH₂CH₂{—}, or the like.

(a) Reaction Mixture

The process commences with formation of a reaction mixture comprising the compound comprising Formula (III) and RCOOH.

(i) Compound Comprising Formula (III)

A variety of compounds comprising Formula (III) may be used in the process. In general, the compound comprising Formula (III) is an alpha amino acid, i.e., the amino and carboxyl groups are attached to the same carbon. The compound comprising Formula (III) may be a natural amino acid, an unnatural amino acid, a standard amino acid, a non-standard amino acid, a proteinogenic amino acid, or a non-proteinogenic amino acid. As detailed above, the identities of R² and Z can and will vary.

In one iteration, R² may be {—}CH₂{—}, {—}CH₂CH₂{—}, or {—}CH(CH₃){—}; and Z may be O. Stated another way, the compound comprising Formula (III) may be serine, homoserine, or threonine, respectively. In another iteration, R² may be {—}CH₂{—} or {—}CH₂CH₂{—}; and Z may be S. In a further iteration, R² may be hydrogen or methyl; R² may be {—}CH₂{—} or {—}CH₂CH₂{—}; and Z may be Se.

(ii) RCOOH

The method comprises contacting the compound comprising Formula (III) with RCOOH. Suitable RCOOH compounds are detailed above in section (I)(a)(ii). The amount of RCOOH contacted with the compound comprising Formula (III) can and will vary. In general, the molar ratio of the compound comprising Formula (III) to RCOOH may range from about 1:1 to about 1:200. In one embodiment, the molar ratio of the compound comprising Formula (III) to RCOOH may range from about 1:5 to about 1:100. In various embodiments, the molar ratio of the compound comprising Formula (III) to RCOOH may be about 1:5, 1:10, 1:15, 1:20, 1:25, 1:30, 1:35, 1:40, 1:45, 1:50, 1:55, 1:60, 1:65, 1:70; 1:75, 1:80, 1:85, 1:90, 1:95, or 1:100. In one embodiment the molar ratio of the compound comprising Formula (III) to RCOOH may be about 1:40.

(iii) Optional Catalyst

In some embodiments, the reaction mixture may further comprise a catalyst. Suitable catalysts and amounts thereof are described above in section (I)(a)(iii).

(b) Reaction Conditions

The process is allowed to proceed under conditions detailed above in section (I)(b). The compounds comprising Formula (III) or Formula (IV) may have L configurations, D configurations, or mixtures thereof.

(III) Preparation of N-Acetyl Homoserine Lactone

In one embodiment, the compound comprising Formula (IV) may be N-acetylhomoserine lactone, and this compound may be prepared as shown in Reaction Scheme 3:

Reaction Scheme 3:

$$HO\diagdown\diagup\underset{NH_2}{\diagdown}\overset{O}{\diagup}OH \xrightarrow{CH_3COOH}$$

$$\underset{O}{\overset{O}{\diagup}}\diagdown\underset{NH}{\diagup}\overset{O}{\diagdown}CH_3$$

For this reaction, the compound comprising Formula (III) is homoserine (i.e., R² is {—}CH₂CH₂{—} and Z is O). RCOOH is acetic acid (i.e., R is methyl).

In general, the molar ratio of homoserine to acetic acid may range from about 1:1 to about 1:200. In various embodiments, the molar ratio of homoserine to acetic acid may range from about 1:5 to about 1:150, from about 1:10 to about 1:100, or from about 1:20 to about 1:50. Typically, the temperature of the reaction may range from about 50° C. to about 160° C. In certain embodiments, the reaction may be conducted at a temperature that ranges from about 70° C. to about 160° C. or from about 120° C. to about 150° C. In some embodiments of the reaction the heat is provided by a conventional heating source known in the art. In other embodiments, heat is provided by microwave irradiation. Generally, the duration of the reaction may range from about 20 minutes to about 48 hours. In some embodiments, the reaction may be allowed to proceed for about 20 minutes to about 4 hours, or from about 8 hours to about 12 hours, or from about 12 hours to about 18 hours.

In one embodiment, the molar ratio of homoserine to acetic acid may be about 1:20, and the reaction may be conducted at about 115° C. for about 16-18 hours. The yield of N-acetyl homoserine lactone may be at least about 80%.

(IV) Preparation of a Compound Comprising Formula (VI)

Also provided herein is a process for preparing a compound comprising Formula (VI). The process comprises contacting a compound comprising Formula (V) with RCOOH, wherein the compound comprising Formula (V) undergoes an N-acylation to form the compound comprising Formula (VI). This aspect of the disclosure is illustrated below in Reaction Scheme 4:

Reaction Scheme 4:

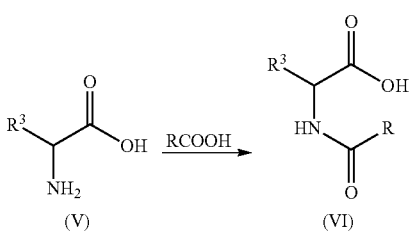

wherein:
R is chosen from hydrogen, hydrocarbyl, and substituted hydrocarbyl; and
$R^3$ is chosen from hydrocarbyl and substituted hydrocarbyl.

In various iterations, R may hydrogen, alkyl, substituted alkyl, haloalkyl, oxoalkyl, carboxy alkyl, aryl, substituted aryl, carboxy aryl, alkenyl, substituted alkenyl, alkynyl, or substituted alkynyl. In certain iterations, $R^3$ may be alkyl, substituted alkyl, haloalkyl, oxoalkyl, carboxy alkyl, aryl, substituted aryl, carboxy aryl, alkenyl, substituted alkenyl, alkynyl, or substituted alkynyl.

(a) Reaction Mixture

The process commences with formation of a reaction mixture comprising the compound comprising Formula (V) and RCOOH.

(i) Compound Comprising Formula (V)

A variety of compounds comprising Formula (V) may be used in the process. In general, the compound comprising Formula (V) is an alpha amino acid, i.e., the amino and carboxyl groups are attached to the same carbon. The compound comprising Formula (V) may be a natural amino acid, an unnatural amino acid, a standard amino acid, a non-standard amino acid, a proteinogenic amino acid, or a non-proteinogenic amino acid. As detailed above, the identity of $R^3$ can and will vary. In one iteration, $R^3$ may be a C1 to C 6 alkyl. In another iteration, $R^3$ may be benzyl.

(ii) RCOOH

The method comprises contacting the compound comprising Formula (V) with RCOOH. Suitable RCOOH compounds are detailed above in section (I)(a)(ii). The amount of RCOOH contacted with the compound comprising Formula (V) can and will vary. In general, the molar ratio of the compound comprising Formula (V) to RCOOH may range from about 1:1 to about 1:200. In one embodiment, the molar ratio of the compound comprising Formula (V) to RCOOH may range from about 1:5 to about 1:100. In various embodiments, the molar ratio of the compound comprising Formula (V) to RCOOH may be about 1:5, 1:10, 1:15, 1:20, 1:25, 1:30, 1:35, 1:40, 1:45, 1:50, 1:55, 1:60, 1:65, 1:70; 1:75, 1:80, 1:85, 1:90, 1:95, or 1:100. In one embodiment the molar ratio of the compound comprising Formula (V) to RCOOH may be about 1:40.

(iii) Optional Catalyst

In some embodiments, the reaction mixture may further comprise a catalyst. Suitable catalysts and amounts thereof are described above in section (I)(a)(iii).

(b) Reaction Conditions

The process is allowed to proceed under conditions detailed above in section (I)(b). The compounds comprising Formula (V) or Formula (VI) may have L configurations, D configurations, or mixtures thereof.

DEFINITIONS

To facilitate understanding of the invention, several terms are defined below.

The term "acyl," as used herein alone or as part of another group, denotes the moiety formed by removal of the hydroxy group from the group COOH of an organic carboxylic acid, e.g., RC(O), wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight chain, branched chain, or cyclic, and include ethenyl, propenyl, isopropenyl, butenyl, isobutenyl, hexenyl, and the like.

The term "alkynyl" as used herein refers to groups having at least one triple bond that contain from two to eight carbon atoms in the principal chain and up to 20 carbon atoms. They may be branched or unbranched, and include propargyl, butynyl, and the like The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The terms "keto acid" or "oxo acid" refer to an acid that has a ketone group as well as a carboxylic acid group.

The "substituted hydrocarbyl," "substituted alkyl," "substituted alkenyl," "substituted aryl," and "substituted heteroaryl" moieties described herein are hydrocarbyl, alkyl, alkenyl, aryl, and heteroaryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, keto, acyl, acyloxy, nitro, amino, amido, nitro, cyano, thiol, ketals, acetals, esters, and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds and processes without departing from the scope of the invention, it is intended that all matter contained in the above description and in the examples given below, shall be interpreted as illustrative and not in a limiting sense.

EXAMPLES

The following examples detail various embodiment of the invention.

Example 1

Synthesis of N-Acetyl Phenylalanine

Phenylalanine (1 g, 6.05 mmol) and acetic acid (20 mL) were mixed together and heated at 150° C. in a microwave for one hour. The excess acetic acid was removed using a rotary evaporator. The residue was taken up in toluene and the solvent was removed using a rotary evaporator. The residue was stirred in methyl t-butyl ether (MTBE) at ambient temperature for one hour. The mixture was filtered and the solid was washed with MTBE. The solid was dried in a vacuum oven at 60° C. The product was obtained as a white solid (983 mg, 78.4%). $^1$H NMR (500 MHz, DMSO-$d_6$) δ ppm 1.79 (s, 3H), 2.84 (dd, 1H), 3.05 (dd, 1H), 4.41 (td, 1H), 7.09-7.33 (m, 6H), 8.20 (d, 1H).

Example 2

Synthesis of N-Acetyl Proline

Proline (1 g, 8.68 mmol) and acetic acid (20 mL) were mixed together and heated at 150° C. in a microwave for two hours. The excess acetic acid was removed using a rotary evaporator. The residue was stirred in MTBE at ambient temperature until a solid precipitated. The mixture was filtered and the solid was washed with MTBE. The solid was dried in a vacuum oven at 60° C. The product was obtained as a white solid (1.12 g, 82.5%). $^1$H NMR (500 MHz, DMSO-$d_6$) δ ppm 1.77-1.95 (m, 4H), 1.97 (s, 2H), 2.0-2.19 (m, 1H), 3.35 (dt, 1H), 3.41-3.58 (m, 2H), 4.19 (dd, 1H).

Example 3

Synthesis of N-Acetyl Valine

Valine (1 g, 8.53 mmol) and acetic acid (20 mL) were mixed together and heated at 150° C. in a microwave for one hour. The excess acetic acid was removed using a rotary evaporator. The residue was stirred in MTBE at ambient temperature for one hour. The mixture was filtered and the solid was washed with MTBE. The solid was dried in a vacuum oven at 60° C. The product was obtained as a white solid (1.13 grams, 83.5%). $^1$H NMR (500 MHz, DMSO-$d_6$) δ ppm 0.74-0.98 (m, 6H), 1.81-1.96 (m, 3H), 1.97-2.18 (m, 1H), 4.13 (dd, 1H), 7.99 (d, 1H).

Example 4

Synthesis of N-Acetyl Homoserine Lactone

Homoserine (20 g, 167.9 mmol) and acetic acid (400 mL) were mixed together. The mixture was heated at 115° C. for 17 hours. The excess acetic acid was distilled from the reaction mixture using a rotary evaporator. The residue was purified by normal phase chromatography using ethyl acetate as the eluent and a 200 g silica gel cartridge. The pure fractions were combined and concentrated. A light-yellow solid (24 g) was obtained. The solid was triturated with refluxing in methyl t-butyl ether. The mixture was cooled to room temperature. The mixture was filtered and the solid was washed with methyl t-butyl ether. A white solid (19.6 g, 81% yield) was obtained.

Example 5

Synthesis of N-Acetyl Homoserine Lactone

Homoserine (1 g, 8.39 mmol), acetic acid (20 mL) were mixed together and heated at 150° C. in a microwave for two hours. The solvent was removed using a rotary evaporator. The residue was purified by normal phase chromatography using ethyl acetate as the eluent and a 12 g silica gel cartridge. The pure fractions were combined and concentrated. The resulting yellow oil was stirred in MTBE at room temperature until the oil solidified. The mixture was filtered and the solid was washed with cold MTBE. The solid was dried in a vacuum oven at 60° C. The product was obtained as a white solid (966 mg, 80.3%). $^1$H NMR (500 MHz, DMSO-$d_6$) δ ppm 1.86 (s, 3H), 2.06-2.21 (m, 1H), 2.31-2.46 (m, 1H), 4.20 (ddd, 1H), 4.28-4.44 (m, 1H), 4.46-4.62 (m, 1H), 8.39 (d, 1H).

Example 6

Synthesis of N-Acetyl Homoserine Lactone

Homoserine (1 g, 8.39 mmol), acetic acid (20 mL), and water (0.5 mL) were mixed together and heated at 150° C. in a microwave for one hour. The solvent was removed using a rotary evaporator. The oily, orange residue was stirred in MTBE until the oil solidified. The mixture was filtered and the solid was washed with cold MTBE. The solid was dried in a vacuum oven at 60° C. The product was obtained as a white solid (1.03 g, 86.1%).

Example 7

Synthesis of N-Propyl Homoserine Lactone

Homoserine (1 g, 8.39 mmol) and propionic acid (20 mL) were mixed together and heated to 150° C. in a microwave for 5 hours. The solvent was removed using a rotary evaporator. The residue was purified by normal phase chromatography using ethyl acetate as the eluent and a 4 g silica gel cartridge. The pure fractions were combined and concentrated. The resulting yellow oil was stirred in MTBE at 0° C. until the oil solidified. The mixture was filtered and the solid was washed with cold MTBE. The solid was dried in a vacuum oven at 60° C. The product was obtained as a white solid (727 mg, 55.1%). $^1$H NMR (500 MHz, DMSO-$d_6$) δ ppm 0.85-1.09 (m, 3H), 2.07-2.22 (m, 3H), 2.34-2.46 (m, 1H), 4.17-4.27 (m 1H), 4.28-4.44 (m 1H), 4.45-4.65 (m, 1H), 8.16-8.40 (m, 1H).

Example 8

Synthesis of N-Acetyl Benzylamine

Benzylamine (1 mL) and acetic acid (20 mL) may be mixed together. The mixture may be heated at 115° C. for 17 hours. The excess acetic acid may be distilled from the reaction mixture using a rotary evaporator. The product may be crystallized from toluene. The mixture may be cooled to 0° C. and then filtered.

What is claimed is:

1. A process for preparing a compound comprising Formula (IV), the process comprising:

contacting a compound comprising Formula (III) with RCOOH to form the compound comprising Formula (IV):

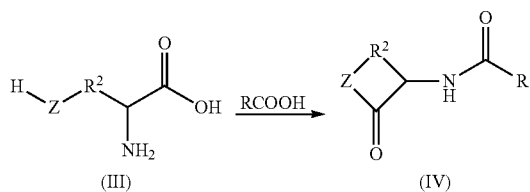

wherein:

R is chosen from hydrogen, hydrocarbyl, and substituted hydrocarbyl;

R² is chosen from {—}CH₂{—}, {—}CH₂CH₂{—} and {—}CH(CH₃); and

Z is chosen from O, S, and Se and; wherein the reaction is conducted at a temperature from about 50° C. to about 160° C.; and, further comprising microwave irradiation.

2. The process of claim 1, wherein the molar ratio of the compound comprising Formula (III) to RCOOH is from about 1:1 to about 1:200.

3. The process of claim 1, further comprising a catalyst chosen from a zeolite chosen from analcime, chabazite, clinoptilolite, heulandite, natrolite, phillipsite, and stilbite, a clay chosen from kaolinite, montmoroillonite, illite and chlorite, and an ammonium salt comprising an organic moiety, the organic moiety being [NH₄]⁺[R'COO]⁻, wherein R' is hydrogen, hydrocarbyl, or substituted hydrocarbyl.

4. The process of claim 3, wherein R' is chosen from hydrogen, methyl, ethyl, propyl, butyl, pentyl, phenyl, benzyl, furyl, allyl, mono-, di-, tri-chloroalkyl, mono-, di-, and tri-fluoroalkyl.

5. The process of claim 1, wherein the compound comprising Formula (IV) has a yield of at least about 60%; and the compounds comprising Formulas (III) and (IV) have an L configuration, a D configuration, or mixture thereof.

6. The process of claim 1, wherein the R² is {—}(CH₂CH₂{—}; Z is O; R is methyl; the molar ratio of the compound comprising Formula (III) to RCOOH is about 1:20; wherein the reaction is conducted at a temperature of about 115° C.; the compound comprising Formula (IV) has a yield of at least about 80%; and the compounds comprising Formulas (III) and (IV) have an L configuration, a D configuration, or mixture thereof.

* * * * *